US006085371A

United States Patent [19]

Umhofer

[11] Patent Number: 6,085,371

[45] Date of Patent: Jul. 11, 2000

[54] LEG SUPPORT APPARATUS

[76] Inventor: Patricia Umhofer, 1692 Tacoma Way #9, Redwood City, Calif. 94063

[21] Appl. No.: 09/383,137

[22] Filed: Aug. 25, 1999

Related U.S. Application Data

[63] Continuation of application No. 09/017,991, Feb. 3, 1998.

[51] Int. Cl.[7] .......... A61F 5/04

[52] U.S. Cl. .......... 5/648; 5/649; 602/15

[58] Field of Search .......... 5/648, 624, 621, 5/630, 649, 651, 650, 661; 297/423.1; 128/845, 882; 602/15, 5, 23, 28

[56] References Cited

U.S. PATENT DOCUMENTS

| | | | |
|---|---|---|---|
| 2,722,692 | 11/1955 | Dempster | 5/648 |
| 3,481,593 | 12/1969 | Allen et al. | 5/648 |
| 3,857,390 | 12/1974 | Harrison | 5/648 |

*Primary Examiner*—Terry Lee Melius
*Assistant Examiner*—Fredrick Conley

[57] ABSTRACT

An apparatus for supporting a leg while healing enhances flow of fluids to and from the leg. The apparatus has an angled leg support area. The various implementations include low cost devices mad from cardboard or the like, re-useable devices made from plastics or wire frames, stackable and foldable devices.

11 Claims, 9 Drawing Sheets

FIG. 4
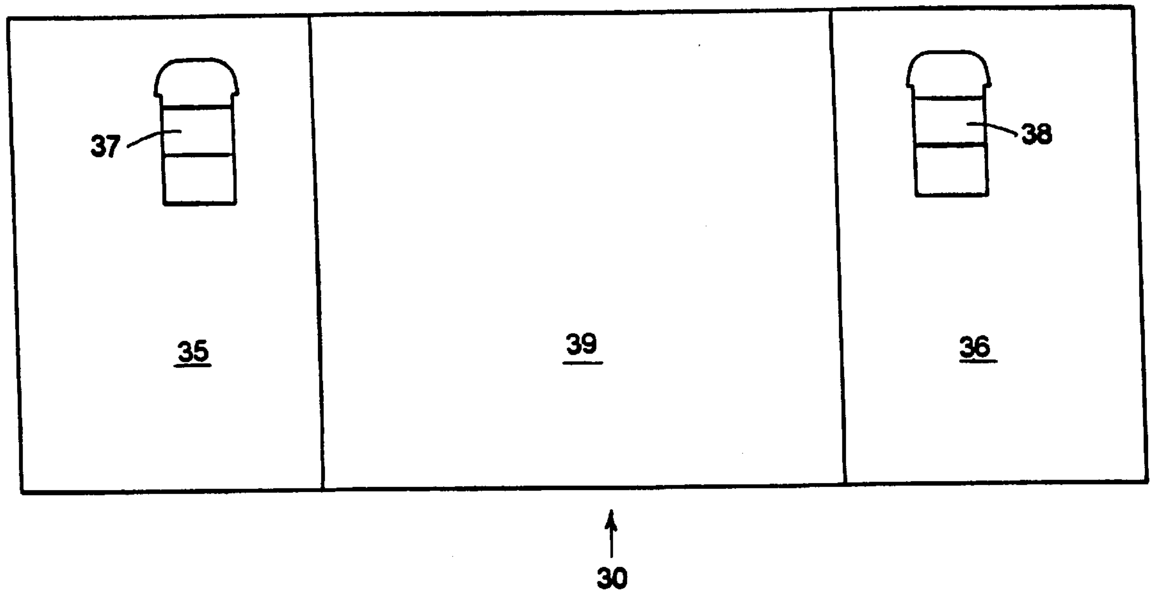
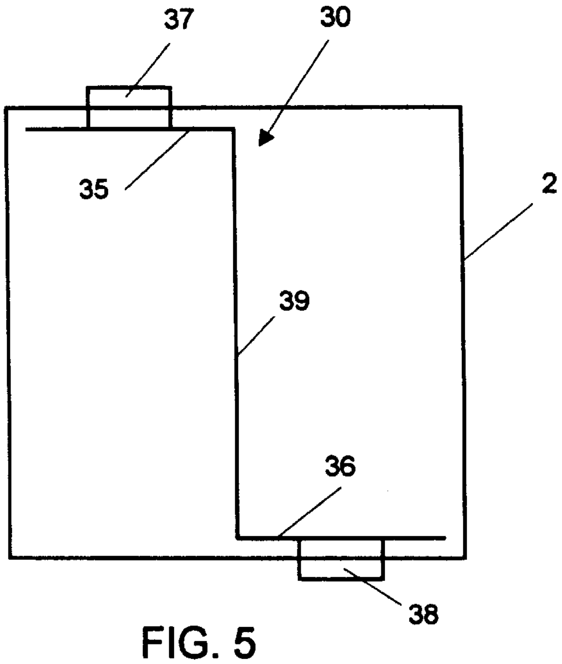
FIG. 5

LEG SUPPORT APPARATUS

This application is a continuation of application Ser. No. 09/017,991 filed on Feb. 3, 1998 pending.

BACKGROUND OF THE INVENTION

One of the critical factors while healing a wound or a break in a leg or foot is to maintain proper blood flow and drainage in the blood vessels and lymphatic system. Improper support of a leg while healing, both with and without a cast, can result in stoppage or reduction of blood flow, thereby causing additional damage or delaying the healing process. In many cases the patient's leg is merely supported by any available pillow. Such a pillow does not ensure that the leg is supported at the proper angle and more importantly at the proper height. Improper support of the leg may also cause discomfort to the resting patient, cause cramps and pain.

These and other disadvantages are overcome by the leg support apparatus of the present invention.

OBJECTS OF THE INVENTION

It is an object of the invention to provide for a leg support which enhances the healing process.

It is an object of the invention to provide for stackable leg support devices.

It is an object of the invention to provide for a stable but inexpensive support for a leg in a cast.

It is another object of the invention to provide for a leg support which is easy to assemble from cardboard cut-outs.

It is still another object of the invention to provide for a biodegradable cardboard leg support.

SHORT DESCRIPTION OF THE DRAWINGS

FIG. 4 is a shape of the cardboard cutout from which the Z-shaped stiffener is formed.

FIG. 5 is a schematic illustration of the fitting of the stiffener of FIG. 4 in the base of the leg support.

SHORT DESCRIPTION OF THE INVENTION

The leg support of the present invention is designed to provide proper control and support to a healing leg in a cast or otherwise while the patient is resting in bed or lying on a couch. The support enhances the healing process by supporting the leg at optimum elevation to allow increased gravitational pull on lymphatic tissues as well as blood fluids to the heart. Proper drainage and blood flow are the key factors in the healing process, especially when no other exercise or only limited exercise is possible to maintain oxygen supply to the extremities furthest from the heart.

Assembling the leg support from simple cardboard cut-outs provides for an economic advantage for short term recovery. Prior to assembly the leg support is easy to transport and store, thereby reducing transport and storage costs for the vendor. Using bio-degradable material eliminates the problems otherwise linked with the disposal of the device.

The shape and form of the leg support of the present invention permits to cover it with other means, such coverings as plastic, foil, cloth etc. to suit the aesthetic desires and hygienic needs of the user.

DETAILED DESCRIPTION OF THE INVENTION

Figure 9:
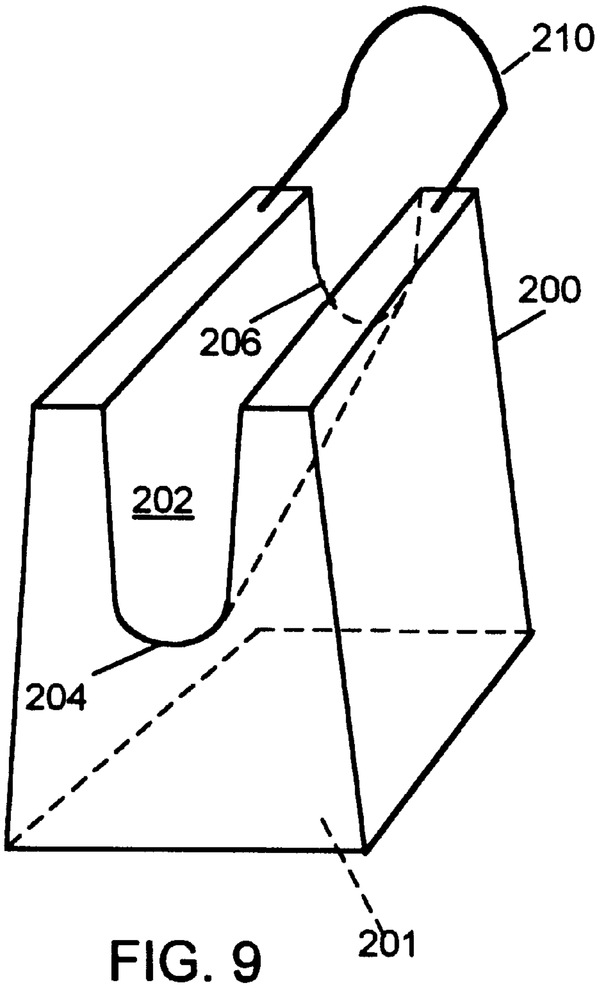
FIG. 9 is an illustration of a stackable leg support device made from cast material.

FIG. 9 is an basic illustration of a leg support device implementing the above features: provide proper control and support to a healing leg in a cast or otherwise while the patient is resting in bed or lying on a couch. Body 200 has a broad base 201 and includes an open space 202, which has a rounded bottom. Front end 204 of space 202 is lower than back end 206 to provide for a slanted support n%wded to enhance fluid flow.

Figure 1A:
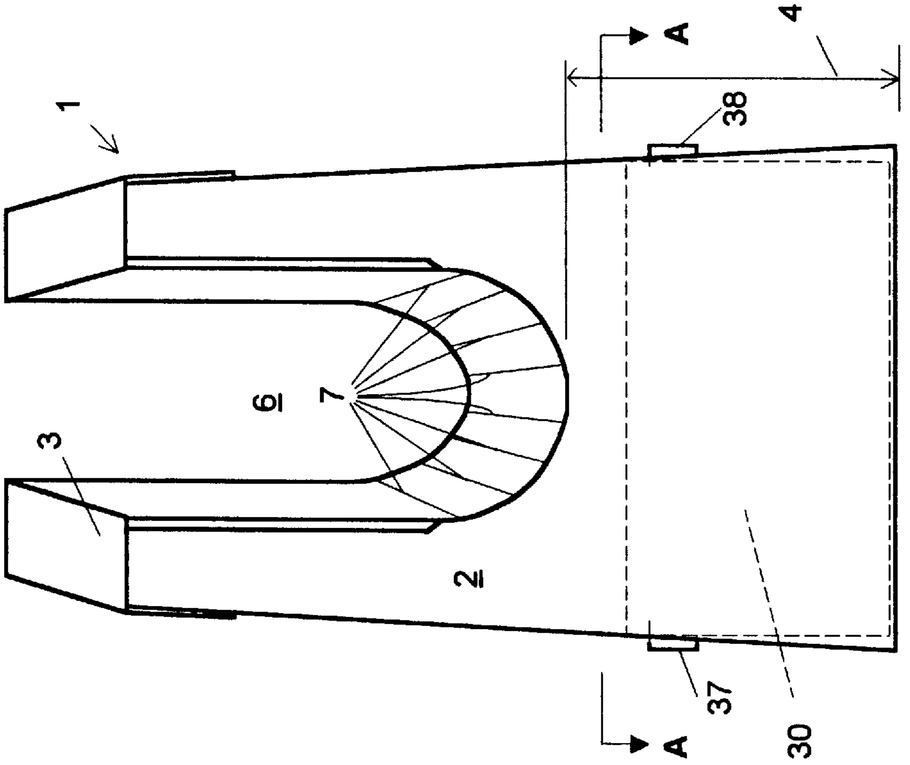
FIGS. 1A and 1B are front and side views of the leg support.
Figure 1B:
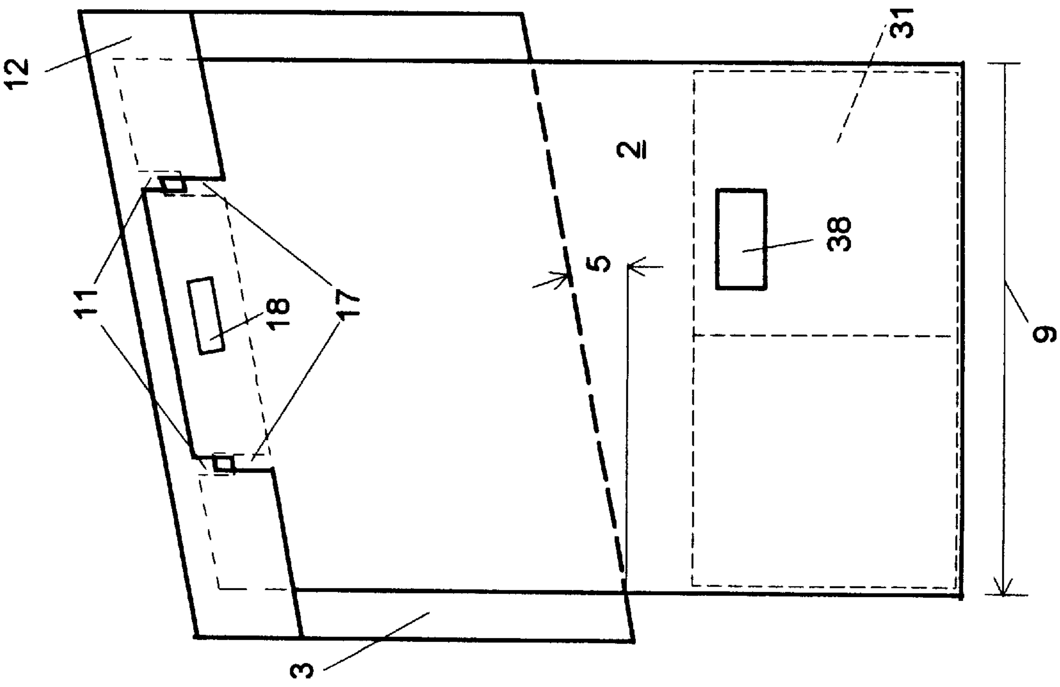
Figure 3:
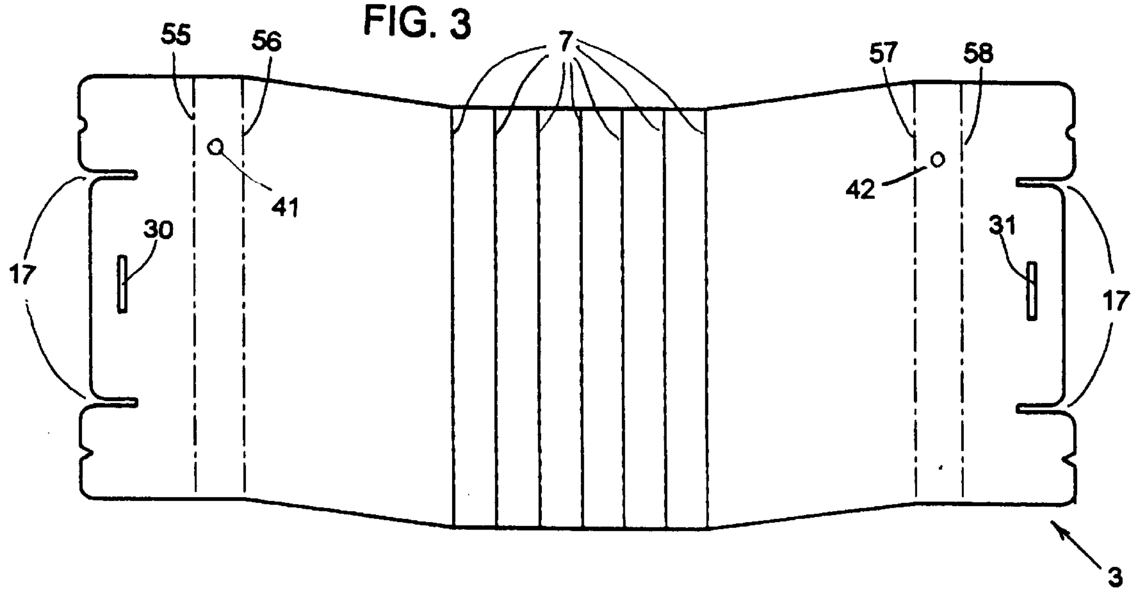
FIGS. 2 and 3 are shapes of cardboard cut-outs from which the leg support is assembled.
Figure 10:
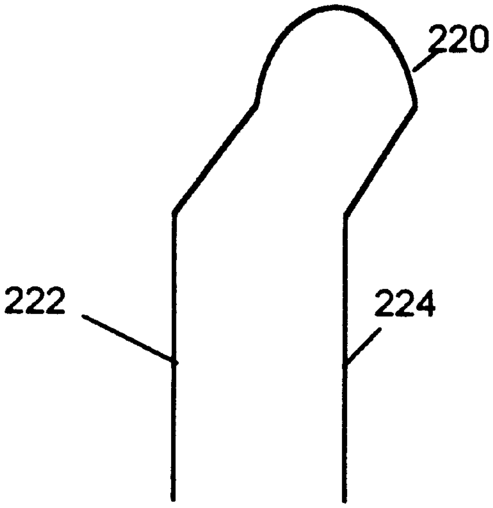
FIG. 10 is an illustration of a blanket support.

An optional fra+w 210 can be used to support a covering blanket and protects the resting foot from the load of such a covering blanket. FIG. 10 is a blanket supporting frame 220, similar to frame 210, which can be used in combination with a leg support as shown in FIGS. 1A and 1B. Insert 3 as shown in FIG. 3 includes holes 41 and 42 through which determine the position of of the upper sections of free ends 222 and 224. Flaps 43 and 44 in base 2 as shown in FIG. 2 have holes for receiving the lower end sections of ends 222 and 224, respectively.

A leg support as shown in FIG. 9 can be manufactured from plastic material using vacuum forming or similar processes which ensure a near even material thickness. Since the outer sides of body 200 as well as the sides of space 202 are slanted, such a leg support device is stackable for easy storage.

FIGS. 1A and 1B are front and side views of the leg support. FIG. 1A is a front view of leg support 1. Leg support 1 includes a base 2 and an insert 3. Base 2 determines height 4 and angle 5 (see FIG. 1B) under which the leg is supported. Insert 3, which is placed into open segments 6A and 6B (not shown) of base 2, has scores 7 to adapt to the semicircular lower end of open segments 6A and 6B to form open space 6. Open space 6 is defined by front open segment 6A and rear open segment 6B (see FIG. 2). As shown in FIG. 1A rear open segment 6B may be narrower than front open segment 6A. Insert 3 is longer than the length 9 of base 2. Base 2 is of rectangular shape and includes openings 11 for receiving folded ends 12 of Ω-shaped insert 3. To maintain a rectangular shape base 1 has bottom fold-ins 22, 23, 24, and 25 (see FIG. 2) which interlock in a known manner. To interlock base 2 with insert 3, interlocking tongues 28 and 29, which are part of base 2, are fitted into slots 30 and 31, resp. (see FIGS. 2 and 3), of insert 3. Item 18 in FIG. 1B depicts the right side interlock.

Figure 2:
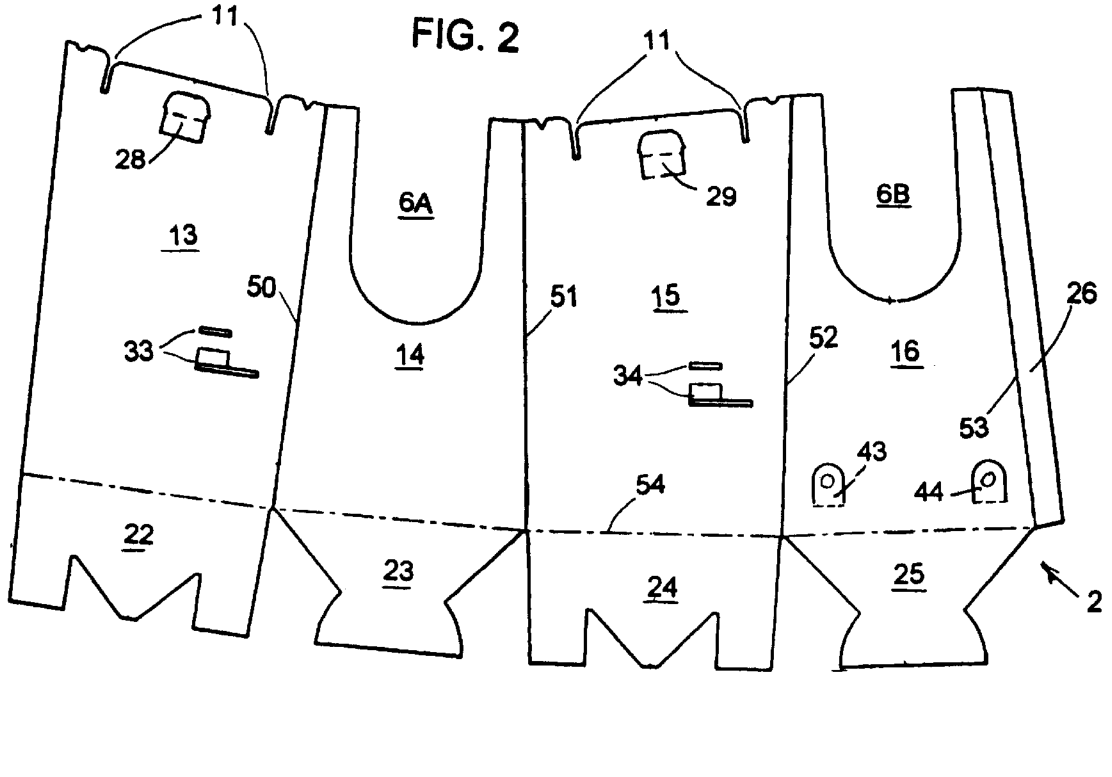

FIGS. 2 and 3 are shapes of cardboard cut-outs from which leg support 1 is assembled. FIG. 2 is the cardboard cutout for base 2. It consists of four sections 13, 14, 15 and 16, each having a bottom section 22, 23, 24, and 25, respectively. Next to side 16 there is a tongue 26 for connecting side 16 to side 13, using glue or staples or the like, to form base 2.

Bottom sections 22, 23, 24, and 25, are folded into each other in a known pattern to provide for a interlocked bottom of base 2.

Lines 50–53 are fold lines between side 13–16, and tab 26 of base 2. Dot-dash line 54 is the fold line between sides 13–16 and bottom sections 22, 23, 24, and 25.

Wells 6A and 6B are the openings into which the actual leg supporting insert 3 (see FIG. 3) is placed. Insert 3 is a near rectangular piece of cardboard with a plurality of score lines 7 to conform to the semicircular bottoms of open segments 6A and 6B, (see FIG. 2). Fold lines 55–58 indicate where 90 degree folds are to be made to bend insert 3 over top ends of base 2. Openings 11 of base 2 and openings 17 of insert 3 match with each other to interlock base 2 with insert 3 on the outside sides of base 2, as illustrated in FIG. 1B.

To maintain rigidness and a rectangular horizontal cross-sectional shape of base 2 a stiffener 30 is placed inside base 2 at the bottom of base 2. This insert 30 has a Z-shape with head and foot 35, 36, resp., and center section 37 and includes tabs 37, 38 for interlocking with base 2 through openings 33 and 34 to secure its position in base 2 close to the bottom of base 2 and well below insert 3 (see FIG. 4).

FIG. 5 is a schematic cross-sectional illustration of the fitting of the Z-shaped stiffener 30 in base 2, as indicated in FIG. 1A by arrowed lined "A—A".

Figure 1C:
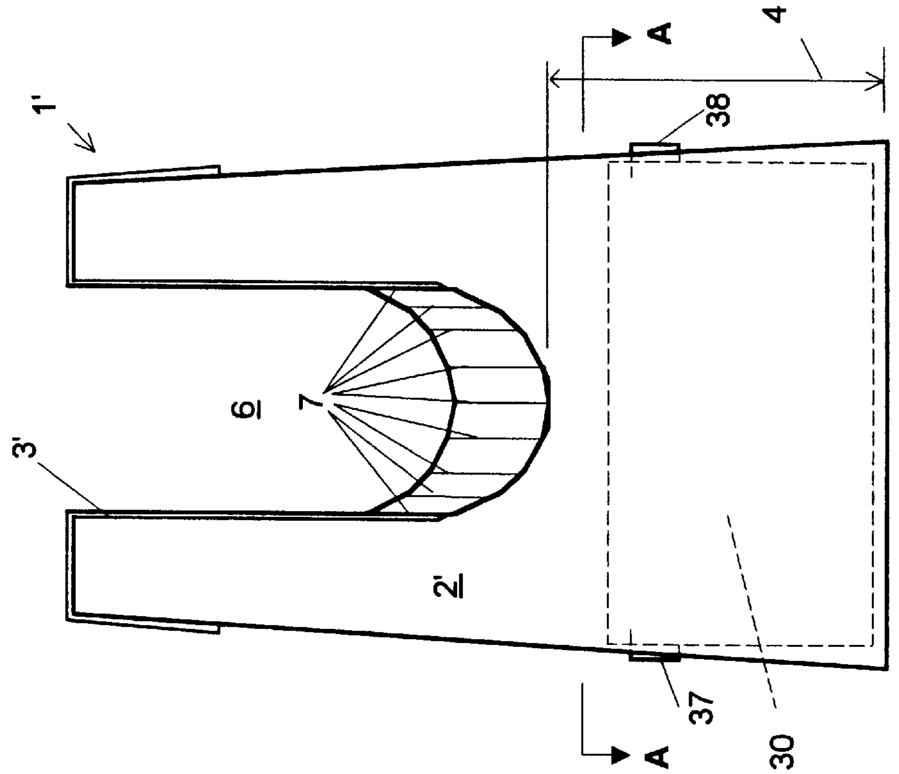
FIGS. 1C and 1D are front and side views of a modified, second version of the leg support.
Figure 1D:
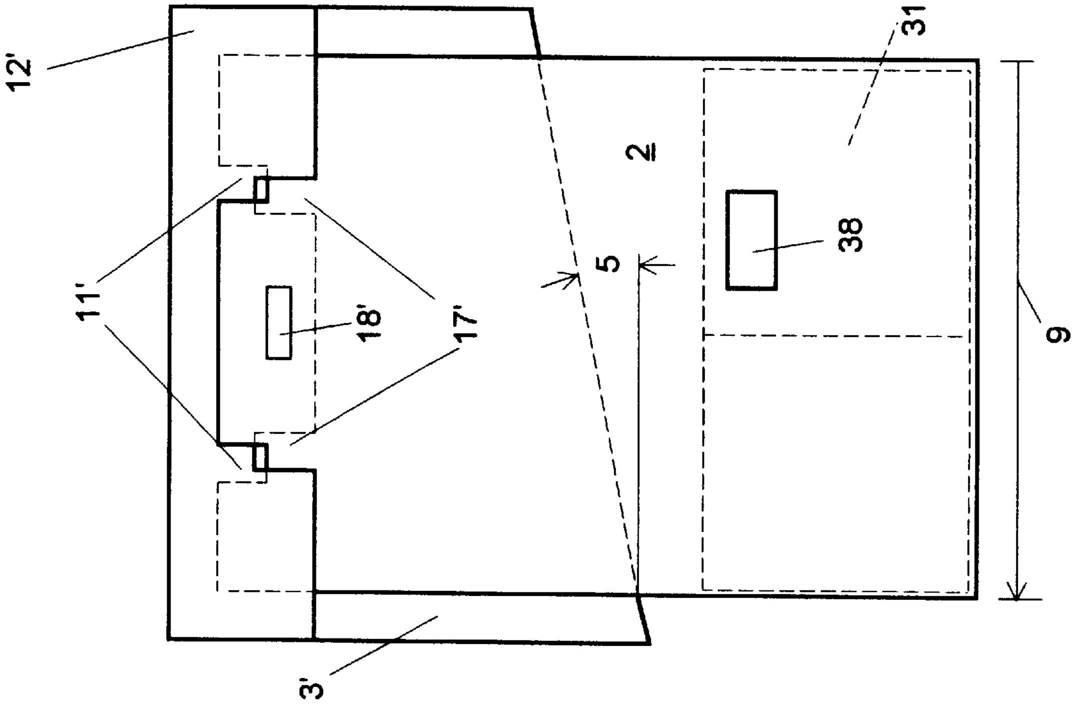

FIGS. 1C and 1D are front and side views of the modified leg support having the same features as the leg support shown in FIGS. 1A and 1B. However, the top edge of the leg support is parallel to the bottom of support base 2. The modification requires slightly different shapes of cardboard cut-outs 2' and 3' when compared with leg support 1'. Items which are cut differently or are at corresponding but different locations, when compared with the leg support shown in FIGS. 1A and 1B, are marked by corresponding primed numbers. These changes are considered to be within the skills of the artisan in this field.

Further, it is considered to be within the skills of the artisan in the field to use other materials than bio-degradable paper based stock for the leg support apparatus or parts thereof to stay within environmental goals. Such other materials may be plastics which can be recycled.

Figure 6A:
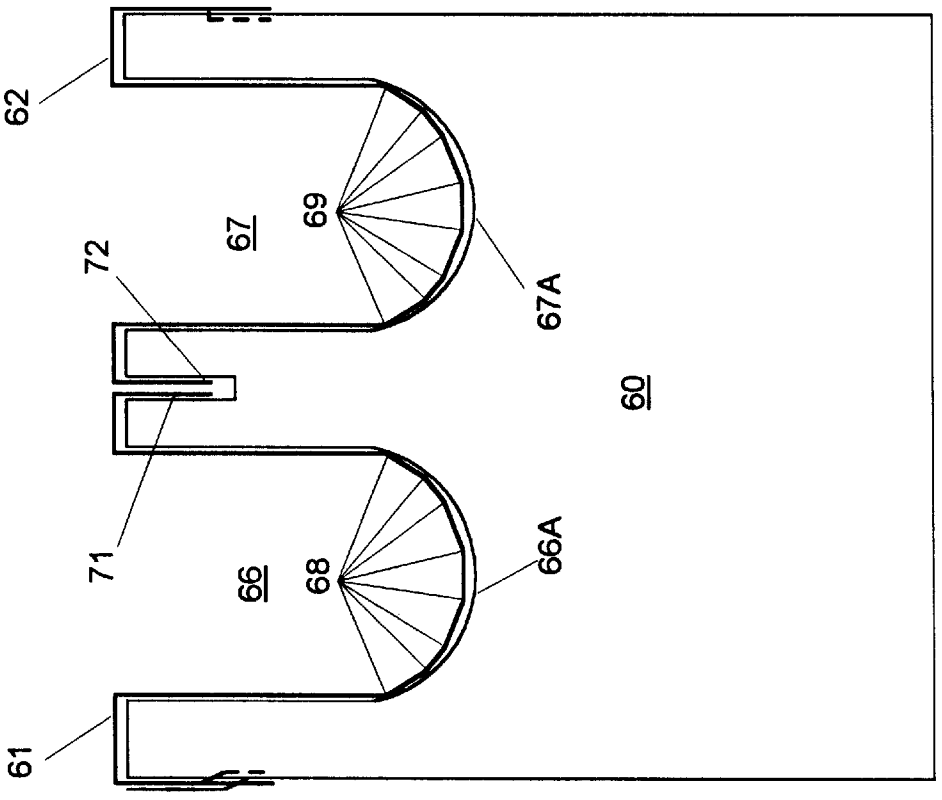
FIGS. 6A and 6B are front and side views of a dual leg support.
Figure 6B:
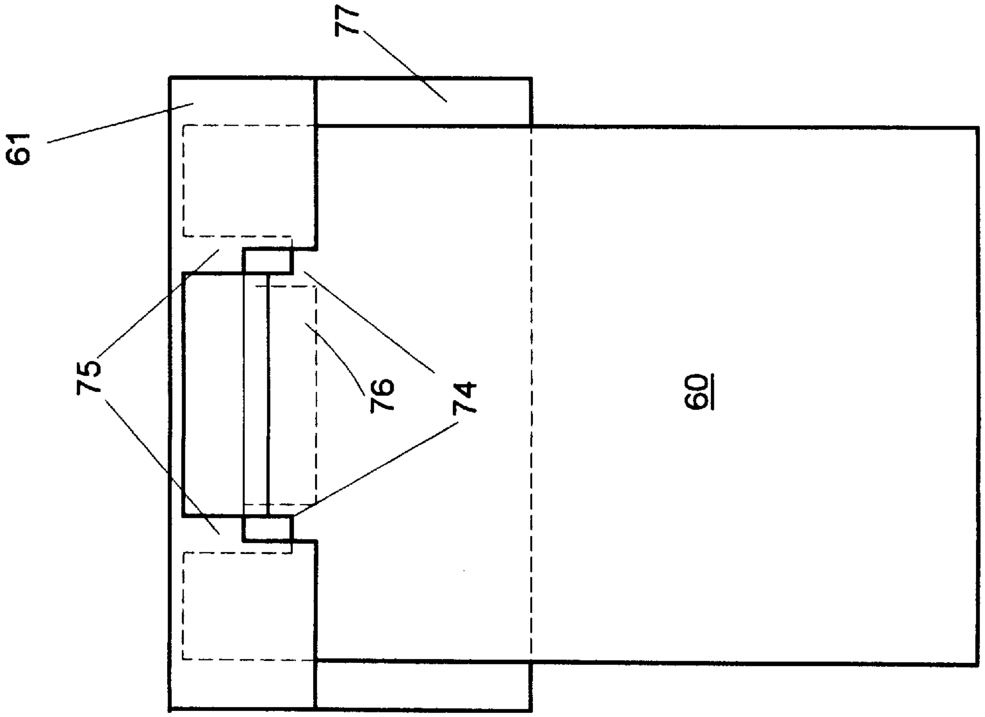

FIGS. 6A and 6B are front and side views of a dual leg support as it is intended for use during medical examination or treatment. Compared with the leg supports if FIGS. 1A–1D the dual leg support does not include an angled support for the legs. The device consists of a base 60, a left insert 61, a right insert 62 and a stiffener 64 inside base 60 to maintain the rectangular cross-section of base 60. Inserts 61 and 62 are mirror images of each other. Base 60 has left open segments 66 and right open segment 67, of which only the front open segments 66A and 67A are shown in FIG. 6A. Insert 61 is placed into open segments 66. Its folds 68 adapts the bottom section of insert 61 to the semicircular lower end of opened segments 66. Insert 62 is placed into open segments 67. Its folds 69 adapts the bottom section of insert 62 to the semicircular lower end of open segments 67. Ends 71 and 72 of inserts 61 and 62, respectively, are placed into center slot 73 of base 60. The second ends of inserts 61 and 62, are inserted with their slots into matching slots of base 60. FIG. 6B illustrates how slots 74 of insert 61 match with slots 75 of insert 61. Section 76 between slots 74 of insert 61 are placed behind section 77 of base 60.

Figure 7A:
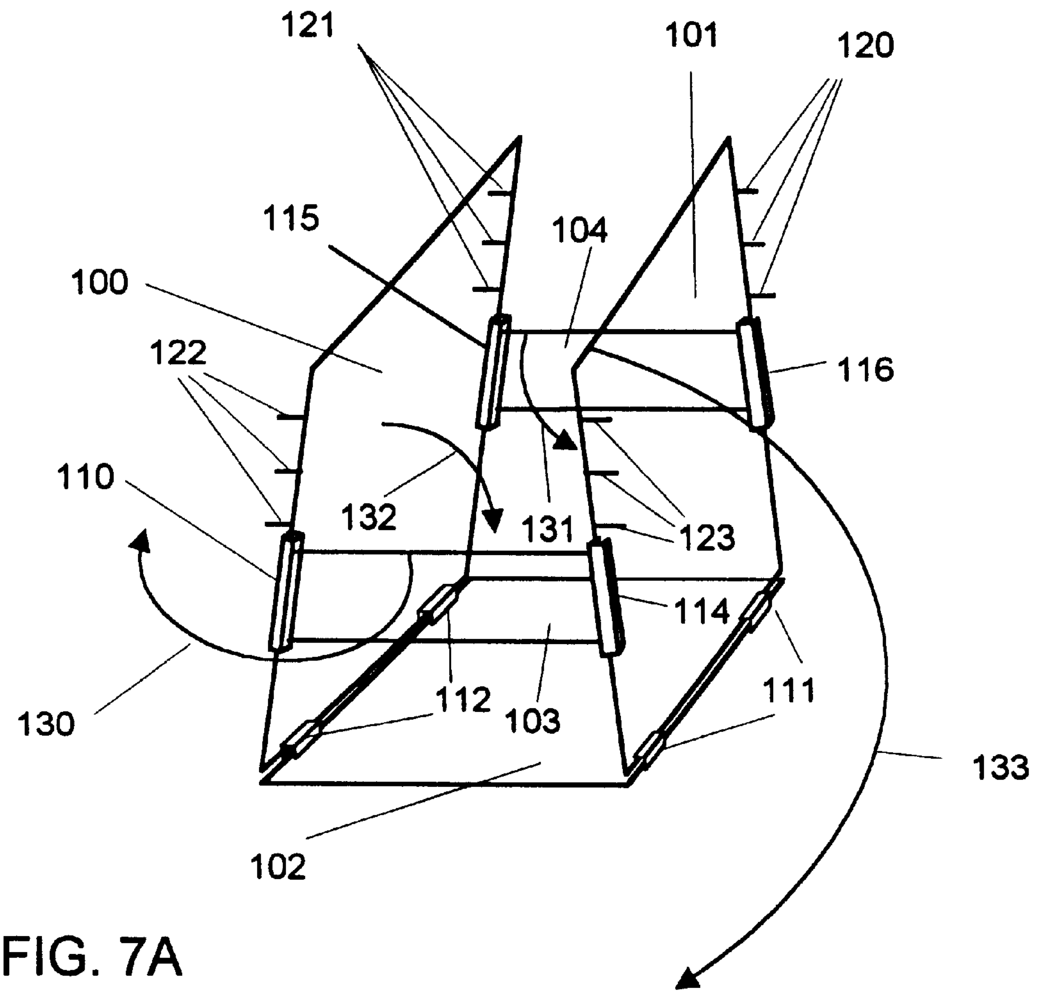
FIGS. 7A and 7B are illustrations of a leg support with a canvas support for the leg and foldable sides.
Figure 7B:
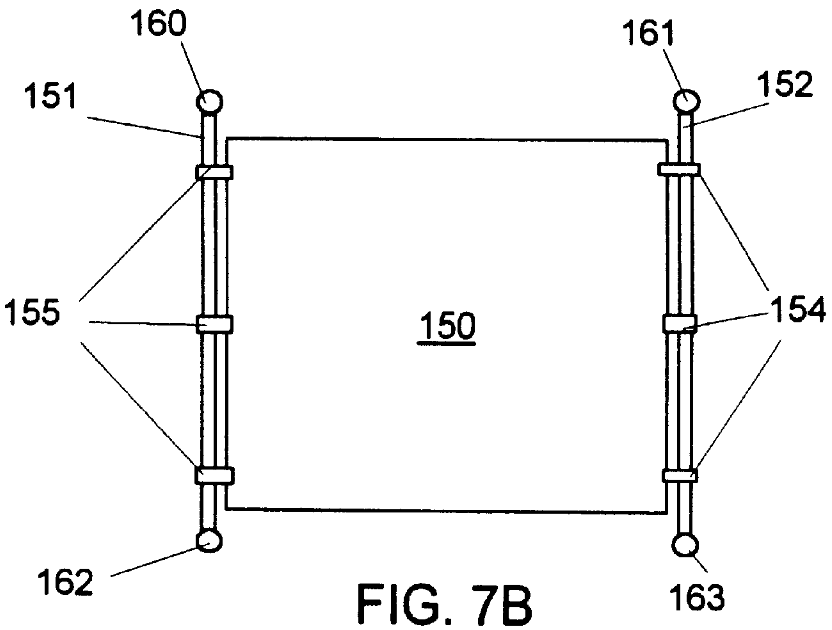

FIGS. 7A and 7B are illustrations of a leg support with foldable sides using a canvas for the support for the leg. FIG. 7A is a perspective illustration of the foldable leg support frame. Left side plate 100 and right side plate 101 are linked to base plate 102 by hinges 112 and 111, respectively. Left side plate 100 and right side plate 101 are held in proper spacing from each other by front gate 103 and back gate 104. Front gate 103 is hinged to left side plate 100 with hinge 110 and links to right side plate by a clamp 114. Back gate 104 is hinged to right side plate 101 with hinge 116 and links to left side plate by a clamp 116. Clamps 114 and 115 are releasable. After release of clamp 114 front gate 103 can be folded over the outside of left side plate 100, as indicated by arrow 100. A released clamp 115 permits to fold back gate 104 over the inside of right side plate 101. As indicated by arrow 133 right side 101 is folded underneath base plate 102. Left side plate 100 is folded over baseplate 102, as indicated by arrow 132. The various side and base plates and gates can be implemented using one plastic plate, whereby the hinges are provided by thin groves in the the plate. In another implementation the various sides are made from wire frames linked by any means known in the trade for hinging wire frames.

FIG. 7B is an illustration of the leg support canvas. A woven cloth or plastic foil 150 is linked to a left and a right rod 151 and 152 using loops 155 and 154, respectively. At the ends of rods 151 and 152 there are mounting rings 160–163. For mounting canvas 150 in the led support frame shown in FIG. 7A holding ring 160 is slipped over one of pegs 121, holding ring 162 is slipped over one of pegs 122, holding ring 161 is slipped over one of pegs 120, and holding ring 163 is slipped over one of pegs 123. The selection of which peg to use from the groups of pegs 120–123, determines the angle at which the leg is supported. Selecting a lower peg raises the respective end of canvas 150.

Figure 8:
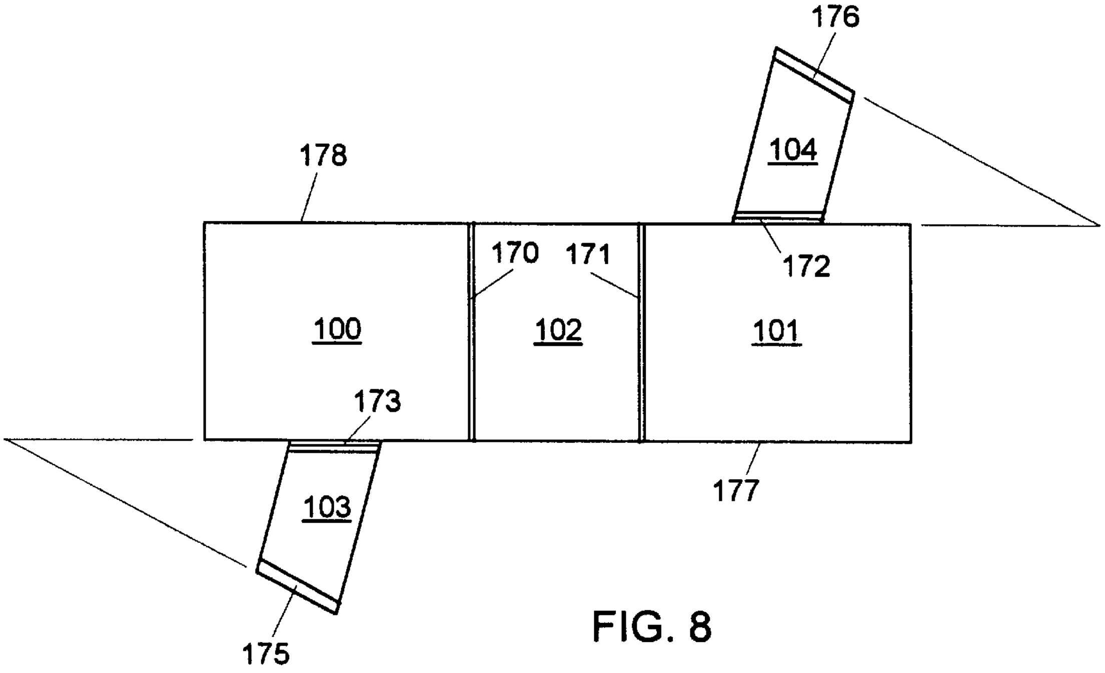
FIG. 8 is a layout of a cut-out or plate made from a plastic sheet for a foldable leg support device

FIG. 8 is a layout of a cut-out or plate made from a plastic sheet for a foldable leg support device as declosed with reference to FIGS. 7A and 7B. The sections of the plate are referenced in accordance with FIGS. 7A and 7B: bottom plate 102, left side plate 100, right side plate 101, front gate plate 103 and rear gate plate 104. The folds between the plate sections have to be made to provide bendability. Folds 170 and 171 must permit an angle of 150°. Folds 172 and 173 must permit bendability of 180° to one side and 90° to the other side relative to the adjacent one of side plates 100, and 101, respectively. Folds 172 and 173 allow to bend the gate plates 103 and 104 under the respective one of side plates 101 and 100. The angles $\alpha$ determine the angle between side plated 100 and 101 when the leg support is set-up. The outside edges of gates plates 103 and 104, include linking means 175 and 176, respectively, with which they interlock with edges 177 and 178 of side plates 101 and 100, respectively, when the leg support is set-up.

Folds can be provides by one or more V-shaped grooves in the plate, or by using separate plates and connect them using hinges. Linking means 175 and 176 can be established by frictional interfaces, pins, screws, or even glue for permanent connection.

Figure 11:
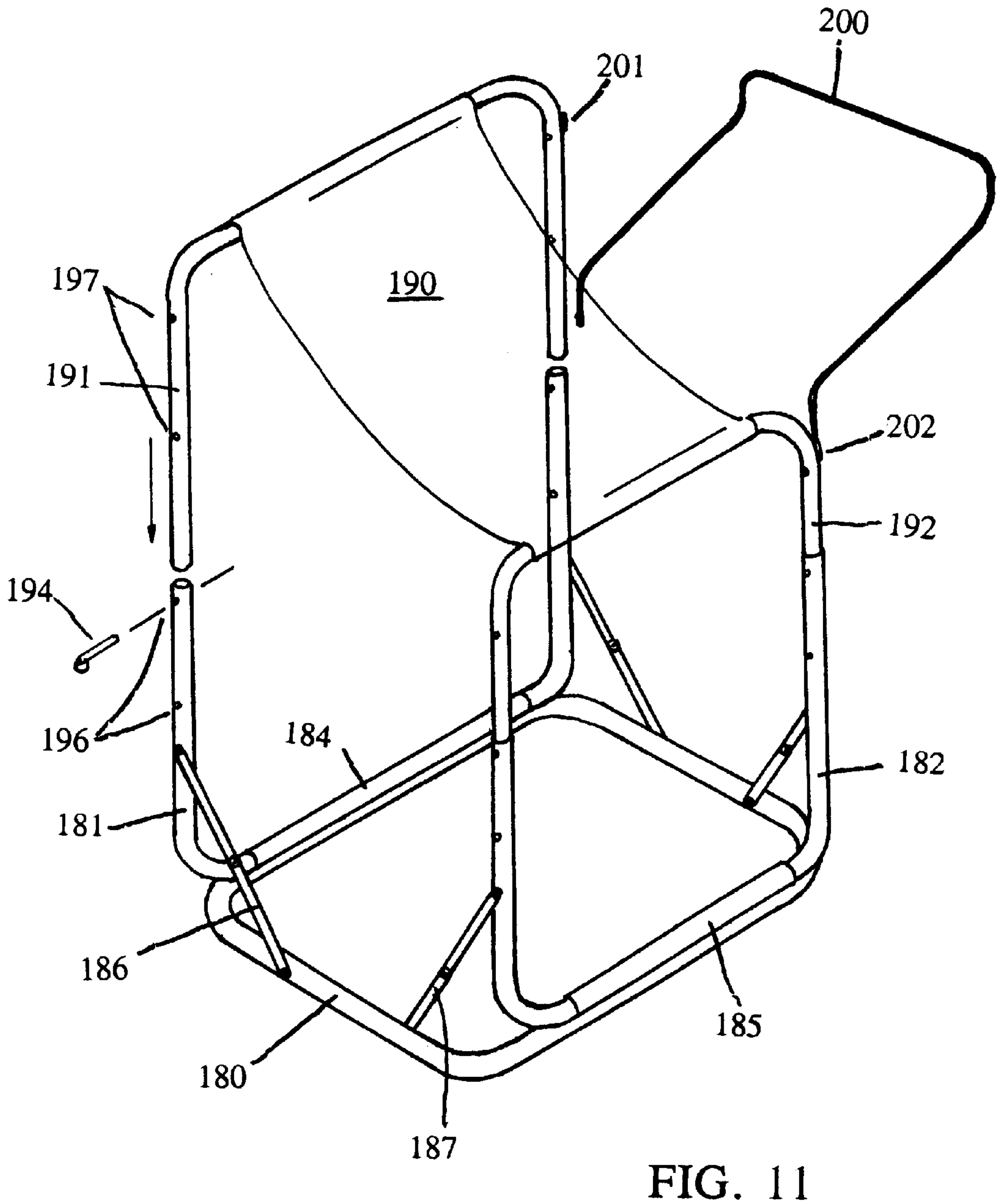
FIG. 11 is an illustration of a second implementation of a foldable leg support device.

FIG. 11 is an illustration of a second implementation of a foldable leg support device. It consists of a base including a base frame 181, a left U-shaped extension receiver 182 and a right U-shaped extension receiver. Left and right extension receivers 182 and 183 are linked to base frame 181 by hinges 184 and 185, respectively. Left and right extension receivers 182 and 183 are also linked to base-frame 181 each by a pair of folding brackets 186 and 187, which secure the position of the extension receivers when they are in the upright position. Extension receiver 181 is wider than extension receiver 182, so that when they fit unto each other when they are folded parallal to base frame 181.

Canvas 190 supports the leg of a patient. Canvas 190 is loosely hanging between extenders 191 and 192. Extender 191 matches extension receiver 181. The height of extender 191 is determined by pins 194, which are placed for a desired height of left side of canvas 190 through holes 196 in extension receiver 181 and holes 197 of extender 191. The height of the right side of canvas 190 is set in a similar fashion using set pins 198. An optional blanket support 200, shown in FIG. 10 with a straight middle section, can be placed in holders 201 and 202.

To provide for a canvas which has front and back at different heights, the canvas can have a trapsoidal shape, being wider at the side which is to be lower, or extenders 191 and 192 can be provided with appropriate bends between the center section and the extender legs.

What I claim is:

1. A support device for a lower leg of a patient during a healing period including a lower leg rest having a recessed rest surface for supporting said lower leg at a desired height and a angle for proper drainage and blood flow, and having a changing width for restricting rotational movement of said lower leg, said recessed rest surface supporting said lower leg from below a knee and including a foot, said support device comprising a rectangular support base having a bottom, two opposing first sides, a front side, and a back side, connecting said first sides, each of said first sides, front side and back side having a top edge; and an insert providing said rest surface and having a proximal edge, a distal edge, and two side ends;

said support base having a first cut-out in said front side, and a second cut-out in said back side for receiving said insert, said first cut-out having two opposing first edges, spaced apart by a first width, and a first rounded lower end connecting said first edges, said second cut-out having two opposing second edges, spaced apart by a second width, smaller than said first width, and a second rounded lower end connecting said second edges, said first rounded lower end of said first cut-out being lower than said second rounded lower end of said back side, thereby determining said angle of said rest surface between said proximal end and said distal end of said insert;

said first width and said second width determining a cross-sectional characteristic of said support surface in longitudinal direction of said support surface;

said insert further having a plurality of first scores between said proximal end and said distal end for adaption to said first shape and said second shape;

said insert, installed in said first and second cut-outs, providing said recessed rest surface and changing from a low position and wide cross-section for receiving the upper end of the lower leg to a higher position and narrower cross-section for receiving the foot of said patient, thereby providing an angled rest surface for proper drainage and blood flow and for limiting rotational movement of said lower leg;

said insert further including second scores in close proximity and parallel to said side ends for folding said side ends over said top edges of said first sides and said top edges of said front side and said back side, and means to removably affix said side ends of said insert to said base.

2. A support device as claimed in claim 1, wherein said support base and said insert are made from bio-degradable material.

3. A support device as claimed in claim 1, wherein said support base and said insert are made from bio-degradable paper-based material.

4. A support device as claimed in claim 1, wherein said support base and said insert are made from bio-degradable corrugated paper-based material.

5. A support device as claimed in claim 1, wherein said support base and said insert are made from folded and scored corrugated paper-based material.

6. A support device as claimed in claim 1, wherein said second sides of said support base are of different heights, and wherein said first sides have top edges connecting said top edges of said second sides.

7. A support device as claimed in claim 1, wherein said first open segment has a first width, said second open segment has a second width, and wherein said first width is larger than said second width.

8. A support device as claimed in claim 1, further including a stiffener in said support base for maintaining a rectangular horizontal cross-section of said support base.

9. A support device as claimed in claim 8, wherein said stiffener includes tabs for securing said stiffener at the bottom of said support base, said support base including openings in said first sides for receiving said tabs of said stiffener.

10. A support device as claimed in claim 1, wherein said support base includes tabs for securing said insert at the top edges of said support base, said insert including openings for receiving said tabs of said support base.

11. A support device for providing rest for two lower legs of a patient during a healing period including two lower leg rests each having a recessed rest surface for supporting one of said two lower leg at a desired height and a angle for proper drainage and blood flow, and having a changing width for restricting rotational movement of said lower leg, each of said recessed rest surfaces supporting one of said lower legs from below a knee and including a foot, support device comprising a rectangular support base having a bottom, two opposing first sides, a fronts side, proximal to said patient, and a back side, distal to said patient sides connecting said first sides, each of said first, said front side and said back side having a top edge; and an insert providing said two lower leg rests and having a proximal edge, a distal edge, and two side ends;

said support base having two first cut-outs spaced apart in said front side, and two second cut-outs spaced apart in said back side for receiving said insert, said first cut-outs each having two opposing first edges, spaced apart by a first width, and a first, rounded lower end connecting said first edges, said second cut-outs each having two opposing second edges, spaced apart by a second width, smaller than said first width, and a second rounded lower end connecting said second edges, said first rounded lower end of said first cut-out being lower than said second rounded lower end of said back side, thereby determining said angle of said rest between said proximal end and said distal end of said insert;

said first width and said second width determining a cross-sectional characteristic of said support surface in longitudinal direction of said support surface;

said insert further having a plurality of first scores between said proximal end and said distal end for adaption to said first shape and said second shape;

said insert, installed in said first and second cut-outs, providing said recessed rest surfaces and changing from a low height and wide cross-section for receiving the upper ends of the lower legs to a higher position and narrower cross-section for receiving the foot of said patient, thereby providing an angled rest surface for proper drainage and blood flow and for limiting rotational movement of said lower leg;

said insert further including second scores in close proximity and parallel to said side ends for folding said side ends over said top edges of said first sides and said top edges of said front side and said back side, and means to removably affix said side ends of said insert to said base;

said support base having two first open segments in one of said second sides and two second open segments in another one of said second sides for receiving said insert, said first and said second open segments extending from said top edges of said second sides to a height for conveniently resting said legs, and having a shape determining a cross-sectional shape of said rest.

* * * * *